United States Patent
Ogino et al.

(10) Patent No.: US 11,373,301 B2
(45) Date of Patent: Jun. 28, 2022

(54) IMAGE DIAGNOSTIC DEVICE, IMAGE PROCESSING METHOD, AND PROGRAM FOR OBTAINING DIAGNOSTIC PREDICTION MODELS USING DEEP LEARNING

(71) Applicant: Hitachi, Ltd., Tokyo (JP)

(72) Inventors: Masahiro Ogino, Tokyo (JP); Yukio Kaneko, Tokyo (JP); Zisheng Li, Tokyo (JP); Yoshihisa Sotome, Tokyo (JP)

(73) Assignee: HITACHI, LTD., Tokyo (JP)

( * ) Notice: Subject to any disclaimer, the term of this patent is extended or adjusted under 35 U.S.C. 154(b) by 118 days.

(21) Appl. No.: 16/803,774

(22) Filed: Feb. 27, 2020

(65) Prior Publication Data

US 2020/0286229 A1    Sep. 10, 2020

(30) Foreign Application Priority Data

Mar. 7, 2019   (JP) ............................. JP2019-041882

(51) Int. Cl.
*G06T 7/00* (2017.01)
*A61B 6/00* (2006.01)
*A61B 5/055* (2006.01)

(52) U.S. Cl.
CPC ............ *G06T 7/0012* (2013.01); *A61B 5/055* (2013.01); *A61B 6/469* (2013.01); *A61B 6/5217* (2013.01);
(Continued)

(58) Field of Classification Search
None
See application file for complete search history.

(56) References Cited

U.S. PATENT DOCUMENTS 11,100,638 B2    8/2021  Ogino et al.
2010/0014780 A1*  1/2010  Kalayeh ................. G06T 5/002
                                             382/284
(Continued)

FOREIGN PATENT DOCUMENTS

CN    105701808 A  *  6/2016
JP    2015-129987 A     7/2015
(Continued)

OTHER PUBLICATIONS

Machine translation of KR-101857624-B1 (Year: 2018).*
(Continued)

*Primary Examiner* — Vu Le
*Assistant Examiner* — Courtney Joan Nelson
(74) *Attorney, Agent, or Firm* — Volpe Koenig

(57) ABSTRACT

An image diagnostic device that obtains a prediction model indicating a higher accuracy diagnosis prediction result includes: an observation unit that collects an image of an examination object; and an image processing unit that generates first image data from the image, and performs image processing of the first image data. The image processing unit is provided with: a feature extraction unit that extracts a first feature from the first image data; a feature transformation unit that converts the first feature to a second feature to be extracted from second image data; and an identification unit that calculates a prescribed parameter value using the converted second feature. The feature extraction unit includes a prediction model learned using a plurality of combinations of the first image data and feature, and the feature transformation unit includes a feature transformation model learned using a plurality of combinations of the first and second features.

20 Claims, 17 Drawing Sheets

(52) U.S. Cl.
CPC ............... *G06T 2207/10116* (2013.01); *G06T 2207/30096* (2013.01)

(56) References Cited

U.S. PATENT DOCUMENTS

| | | | | |
|---|---|---|---|---|
| 2014/0375671 A1* | 12/2014 | Giger | ................... | G06T 7/0014 345/589 |
| 2016/0093050 A1* | 3/2016 | Kim | ....................... | G06K 9/46 382/128 |

FOREIGN PATENT DOCUMENTS

| | | | |
|---|---|---|---|
| JP | 2017-045341 A | | 3/2017 |
| JP | 2019-025044 A | | 2/2019 |
| KR | 20180040287 A | * | 4/2018 |
| KR | 101857624 B1 | * | 5/2018 |

OTHER PUBLICATIONS

Machine translation of KR-20180040287-A (Year: 2018).*
Machine translation of CN-105701808-A (Year: 2016).*
Singanamalli, Asha et al. "Identifying In Vivo DCE MRI Markers Associated With Microvessel Architecture and Gleason Grades of Prostate Cancer," Journal of Magnetic Resonance Imaging, vol. 00, No. 00, 2015 Wiley Periodicals, Inc. (pp. 1-10).
Burnside, Elizabeth, S. et al., "Using Computer-Extracted Image Phenotypes From Tumors on Breast Magnetic Resonance Imaging to Predict Breast Cancer Pathologic Stage" Cancer, Mar. 1, 2016 (pp. 748-757).
Japanese Office Action dated Feb. 8, 2022 for Japanese Patent Application No. 2019-041882.

* cited by examiner

IMAGE DIAGNOSTIC DEVICE, IMAGE PROCESSING METHOD, AND PROGRAM FOR OBTAINING DIAGNOSTIC PREDICTION MODELS USING DEEP LEARNING

INCORPORATION BY REFERENCE

The present application claims priority from Japanese patent application JP-2019-41882 filed on Mar. 7, 2019, the content of which is hereby incorporated by reference into this application.

BACKGROUND OF THE INVENTION

Field of the Invention

The present invention relates to an image diagnostic device such as a magnetic resonance imaging (hereinafter, MRI) device, a CT device, and an ultrasound imaging device, and specially relates to image processing for performing a high-level diagnosis using the image diagnostic device.

Background Art

In recent years, as image diagnosis support techniques by Artificial Intelligence (AI), methods of predicting the presence or absence of or the malignancy (grade) of a disease (for example, tumor) using Deep Learning (DL) have been proposed. In DL, a convolution neural network (CNN) learned so as to classify images into a plurality of categories is generally used.

As one example of a method of predicting the grade of a tumor using DL, a document 1: Asha Singanamalli, et al., "Identifying in vivo DCE MRI markers associated with microvessel architecture and gleason grades of prostate cancer.", Journal of Magnetic Resonance, 2015, 43, p. 149-158, presents a prediction model in which a plurality of image features are acquired from each of image data imaged by dynamic contrast-enhanced MRI (DCE-MRI) and pathological image data, and a map in which the each features are combined is generated, and from the map, a relation with Gleason score (GS) information used in stage calculation of prostate cancer is analyzed, thereby estimating GS relative to a new input image.

Moreover, US 2014/0375671 discloses a method in which a plurality of image features of an MRI image are extracted, and a map in which the image features are arrayed for each feature is presented. This map image is generated by analyzing relationships between a plurality of features and a plurality of clinical conditions (malignancy and the like) to allow information on a clinical condition to be associated with an MRI image of a subject.

However, in order to obtain a diagnosis result using the technique of the aforementioned document 1, in addition to an examination by an image diagnostic device, a pathological examination to acquire a pathological image of an examination site is necessary. A needle or the like is used to collect a minute tissue of a patient in the pathological examination, which puts a large physical burden on the patient, so that a technique that can determine the presence or absence and the grade of a tumor without conducting a pathological examination is desired. From another viewpoint, a technique that can accurately determine an actual target of a pathological examination to be performed can provide optimal medical treatment.

Moreover, when the technique of US 2014/0375671 is used, a relationship between a feature of an image and a clinical condition is derived from analyses of a large amount of data, so that it is difficult to indicate the adequacy from a medical viewpoint. In other words, when the technique is used in the actual medical treatment field, there is a high possibility that the processing content being in a black box causes a problem.

As a method of predicting and presenting a property of a tumor that can be determined from an image of an image diagnostic device in a pathological diagnosis without conducting a pathological examination, in document 2: Elizabeth S. Burnside, et al., "Using computer extracted image phenotypes from tumors on breast magnetic resonance imaging to predict breast cancer pathologic stage.", Cancer, 2016, p. 748-757, discloses a method of predicting a pathological image finding from an input of an image diagnostic device image, by learning a large combination of an image diagnostic device image and a pathological diagnosis result (finding, text information).

SUMMARY OF THE INVENTION

The method as disclosed in the document 2 can predict and present findings (tumor malignancy, grade, and the like) that are obtained from a pathological diagnosis using a medical image without conducting a pathological examination. However, this method is a method of deriving a relationship between an image and a text, that is, an image diagnostic device image and a pathological finding, from analyses of a large number of data, and an explanation of the adequacy from a medical viewpoint is difficult. Moreover, in this method, a learning model as a learning sample is created using a combination of different information levels, that is, an image diagnostic device image and a pathological finding (text), so that the correlation relation becomes a black box, and the infallibility of a prediction result cannot be verified.

An object of the invention is to obtain a diagnosis prediction model indicating a prediction result with higher accuracy and with high medical adequacy, using DL.

In order to solve the abovementioned problem, in the invention, processing is performed by obtaining image data from an image signal of an image acquired by an observation unit, extracting a first feature from this image data, thereafter converting the first feature to a second feature, and calculating a prescribed parameter using the second feature.

Specifically, the image diagnostic device includes an observation unit that collects an image signal of an examination object; and an image processing unit that generates first image data from the image signal, and performs image processing of the first image data. The image processing unit is provided with: a feature extraction unit that extracts a first feature from the first image data; a feature transformation unit that converts the first feature to a second feature to be extracted from second image data; and an identification unit that calculates a prescribed parameter value using the converted second feature. The feature extraction unit includes a prediction model learned using a plurality of combinations of the first image data and the first feature, and the feature transformation unit includes a feature transformation model learned using a plurality of combinations of the first feature and the second feature.

With the invention, it is possible to calculate a parameter value to be used in a more highly accurate diagnosis, using image data that is generated from the image signal collected by the observation unit. This can implement a diagnosis by using the image diagnostic device with higher accuracy, and contribute in medical quality enhancement.

DETAILED DESCRIPTION OF THE INVENTION

The invention is applicable to various kinds of image diagnostic devices, such as MRI devices, CT devices, and ultrasound imaging devices, each of which is provided with an observation unit and an image processing unit. Firstly, an embodiment having a configuration common to respective modalities will be described.

First Embodiment

Figure 1:
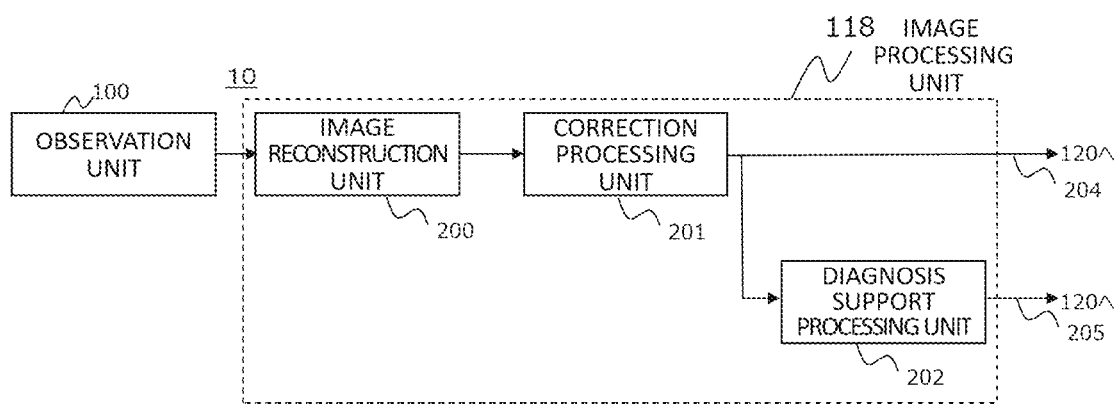
FIG. 1 is a diagram illustrating an overall configuration of an image diagnostic device in a first embodiment.

An image diagnostic device 10 according to the present embodiment is provided with, as illustrated in FIG. 1, an observation unit 100 that collects an image signal necessary for image reconstruction from a subject, and an image processing unit 118 that performs image processing of the subject imaged by the observation unit 100. The image diagnostic device 10 is further provided with, in an inside or an outside thereof, an input unit 119 with which various kinds of instructions are input, an output unit 120 such as a display, and a storage device 121 (for example, see FIG. 15).

The observation unit 100, although the configuration thereof differs depending on the modality, acquires an image signal by the measurement of the subject, and passes the acquired image signal to the image processing unit 118. The detailed configuration for each modality will be described in embodiments, which will be described later.

The image processing unit 118 is provided with an image reconstruction unit 200 that reconstructs an image of image data (first image data) from the image signal received from the observation unit 100, a correction processing unit 201 that performs correction processing (for example, noise correction) of the image using the generated image data, and a diagnosis support processing unit 202 that performs processing of supporting an image diagnosis using the image data of the correction-processed image. Image data of a correction-processed image 204 and image data of an image 205 processed by the diagnosis support processing unit 202 are output to the output unit 120 (see FIG. 11).

Figure 2:
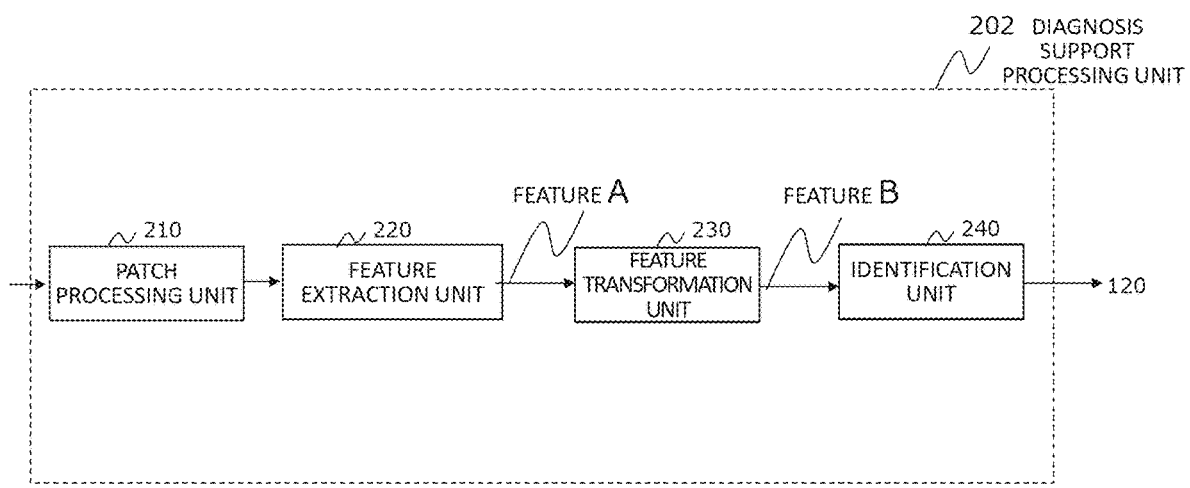
FIG. 2 is a diagram illustrating a configuration of a diagnosis support processing unit in the first embodiment.

The diagnosis support processing unit 202 is provided with, as illustrated in FIG. 2, a feature extraction unit 220 that extracts a first feature A from the first image data received from the correction processing unit 201 using a prediction model, a feature transformation unit 230 that performs transformation processing of the first feature A to a second feature B using a feature transformation model, and an identification unit 240 that calculates a prescribed parameter value from a second feature B using an identification model.

The feature A is a feature that is extracted from an image (hereinafter, referred to as input image) to be obtained from the image signal acquired by the observation unit 100, and is a result in which DL has been caused to learn luminance information on a lesion site, for example. The feature B is a feature that is extracted from second image data having more detailed information than the first image data from which the feature A is extracted, and is a result in which DL is caused to learn information (feature) in the same site of a pathological image as that of the input image, for example. Examples of the parameter calculated by the identification unit 240 from the feature B include the presence or absence of a tumor that is diagnosed from the pathological image, the grade thereof, and the stage of a disease other than the tumor.

When the image data received from the correction processing unit 201 is divided into patches of predetermined size, and is processed for each patch, the image processing unit 118 is further provided with a patch processing unit 210 that cuts at least one patch from the image data received from the correction processing unit 201. In that case, the patch processing unit 210 passes the cut patch to the feature extraction unit 220, the feature extraction unit 220 extracts the feature A for each patch, the feature transformation unit 230 converts the feature A to the feature B, and the identification unit 240 identifies a parameter from the feature B, and outputs, after integrating the processed patch data, the integrated data to the output unit 120.

Figure 15:
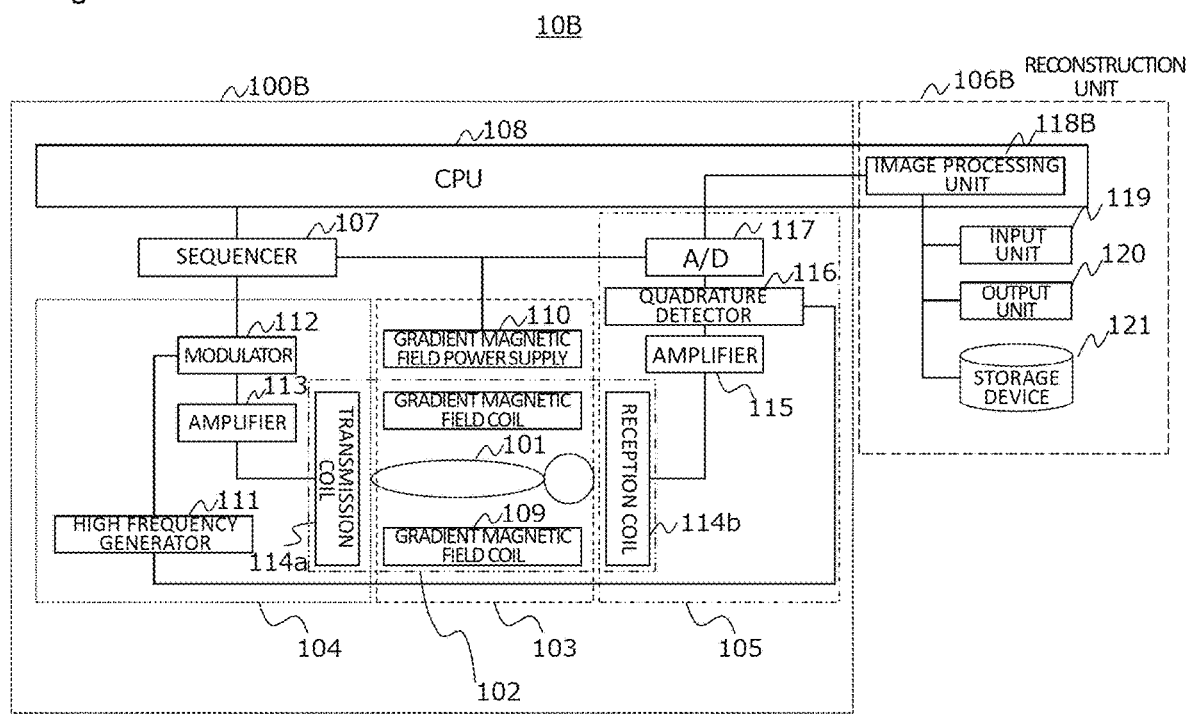
FIG. 15 is a diagram illustrating an overall configuration of an image diagnostic device (MRI device) in a second embodiment.

Data and a program that are necessary for the processing in the image processing unit 118 are stored in the storage device 121 (FIG. 15 and the like). The data necessary for the processing in the image processing unit 118 specifically includes later-described respective learning models and the like that are used in the processing to be performed by the feature extraction unit 220, the feature transformation unit 230, and the identification unit 240. The storage device 121 may be a server device of a workstation communicably connected to the image diagnostic device 10 via a network or that of picture archiving and communication systems (PACS), or may be a portable storage medium that can be connected to the image diagnostic device 10. Moreover, as an alternative to the storage device 121, as a mechanism of storing each data, a cloud connected to the observation unit 100 via the network may be used.

When the image diagnostic device is provided with a CPU or a GPU as a computation unit or a control unit, the function of the image processing unit 118 is implemented as software that is mounted on the CPU or the GPU. Specially, the feature extraction unit 220, the feature transformation unit 230, and the identification unit 240 are implemented as a neural network including a learning function, and a publicly known software package such as CNN can be used. Moreover, a part of the function of the image processing unit 118 can be implemented by hardware such as an application specific integrated circuit (ASIC) or a field programmable gate array (FPGA).

Hereinafter, an operation of the image processing unit 118 in a case where from an input image (first image), as one example of a parameter of a pathological image (second image), the grade of a tumor is calculated for each patch will be described. Before the explanation for a procedure of processing an image of a subject by the image processing unit 118, learning models to be incorporated into the diagnosis support processing unit 202 will be firstly described.

[Details of Learning Models]

Three types of learning models below are used in the embodiment, and a CNN is used in each learning model. The first learning model is a prediction model for extracting the feature A from image data of an input image by the feature extraction unit 220, the second learning model is a feature transformation model for converting the feature A to the feature B by the feature transformation unit 230, and the third learning model is an identification model for calculating a prescribed parameter from the feature B by the identification unit 240.

Firstly, the prediction model for extracting the feature A will be described. The prediction model is a model learned using combinations of an input image and a lesion presence or absence (benign/malignant) label as data for learning.

Figure 3:
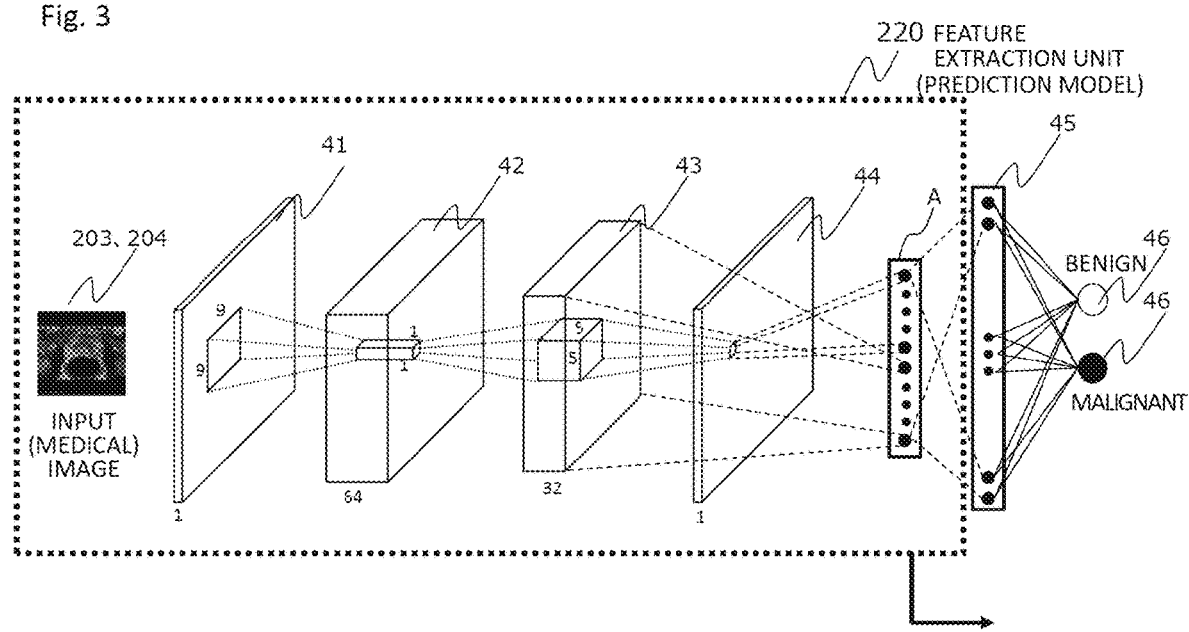
FIG. 3 is a diagram illustrating an example of a structure of a feature extraction unit (CNN)
Figure 4:
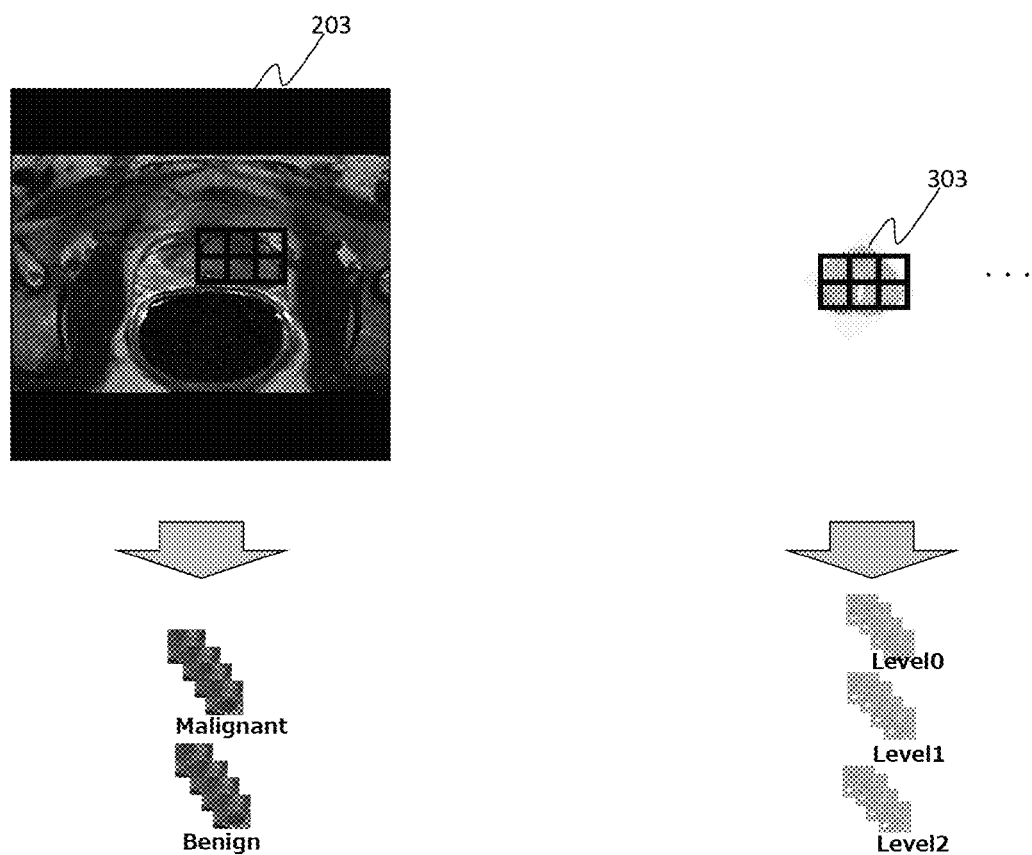
FIG. 4 is a diagram for explaining patch processing between an input image and a pathological image.

As schematically illustrated in FIG. 3, the CNN in the prediction model is a computing unit that is configured to repeat a large number of convolution computations 42 and pooling 43 between an input layer 41 and an output layer 44 on a multilayer network and is to be constructed on a computer. The CNN of the prediction model repeats the convolution computation and the pooling with regard to input data (FIG. 4) which is an input image 203 for learning divided into a plurality of patches by the patch processing unit 210, thereby extracting the feature A (for example, 1024 dimensions) for identifying the presence or absence of a lesion in the input image 203 with high accuracy. In FIG. 3, a numeric character in front of a block indicating each layer is the number of layers, and a numeric character in each layer represents the size to be processed in the layer. It should be noted that as for the feature A, which is divided into a plurality of classifications 45 necessary for a diagnosis, parameters 46 (for example, whether the tumor is benign or malignant) can be calculated from the classifications 45.

Figure 5:
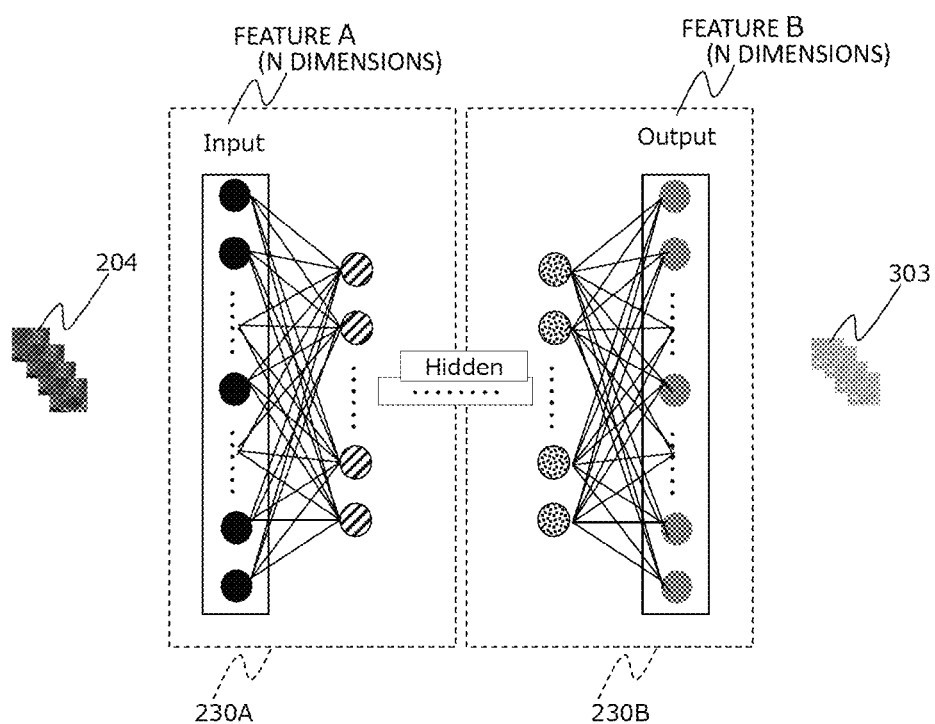
FIG. 5 is a diagram illustrating an overview of a structure of a feature transformation unit (CNN)

Next, the feature transformation model that converts the feature A to the feature B will be described. The feature transformation model includes, as illustrated in FIG. 5, two networks of an encoder 230A and a decoder 230B, and is a model learned using a plurality of combinations of the feature A and the feature B as data for learning. This feature transformation model is incorporated into the feature transformation unit 230 such that when the feature A of the input image 204 extracted from the feature extraction unit 220 is input to the encoder 230A, the feature B of a pathological image 303 is output from the decoder 230B. This diagram illustrates an example in which both of the feature A and the feature B have N dimensions (N is a natural number). The characteristic point of the feature transformation model is that the feature transformation model is not a model in which a relationship between an image and a text was learned as the prior research (the document 2), but a model in which a relationship between an image and an image was learned, and was further learned between features with the high level of abstraction using DL.

Figure 6:
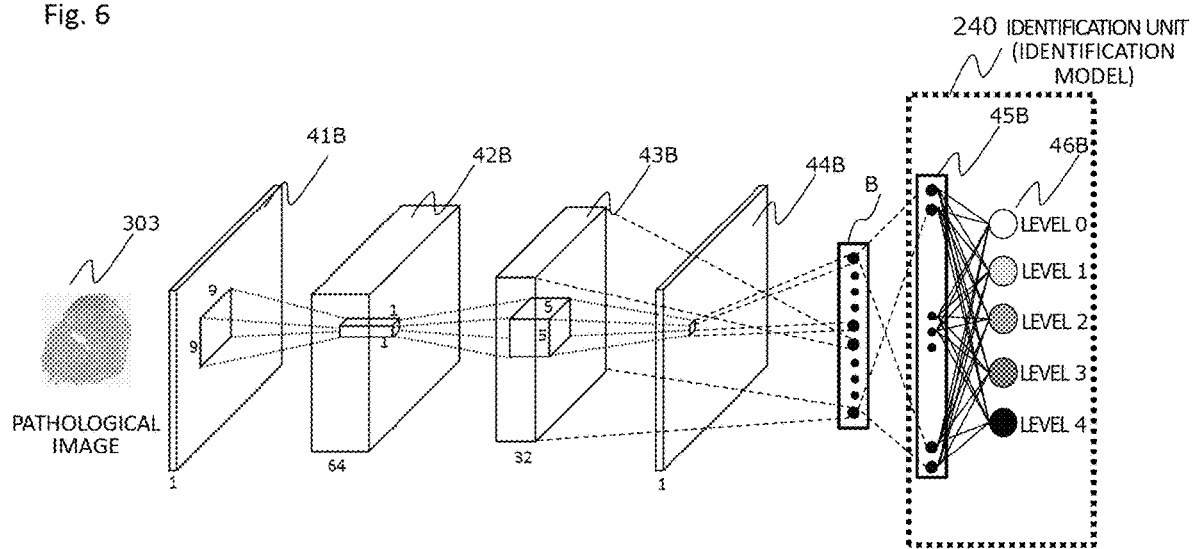
FIG. 6 is a diagram illustrating an example of a learning structure (CNN) in which a feature B is extracted from the pathological image, and a structure of an identification unit.

The feature B for learning that is used in the feature transformation model is extracted from the pathological image 303 for learning (FIG. 4) generated from a pathological examination of the subject and patch-processed, by a CNN. This CNN that extracts the feature B for learning from the pathological image 303 for learning is also included in the feature transformation unit 230. The CNN that extracts the feature B for learning from the pathological image 303 for learning is a CNN similar to the CNN of the prediction model, and is, specifically as illustrated in FIG. 6, a computing unit that is configured to repeat convolution computations 42B of a large number and pooling 43B of a large number on the multilayer network between an input layer 41B and an output layer 44B and is constructed on the computer, and repeats the convolution computations and the pooling with regard to the pathological image 303, thereby extracting the feature B for learning (for example, 1024 dimensions) for identifying the grade of a tumor portion in the pathological image 303 with high accuracy, for example.

Figure 7:
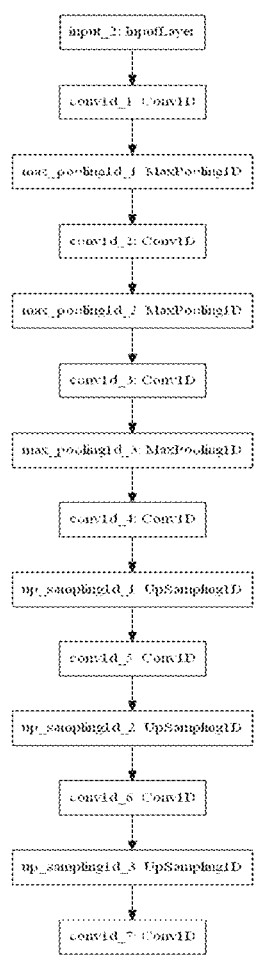
FIG. 7 is a diagram illustrating a detail of the structure of the feature transformation unit.

The CNN of the feature transformation model has a multilayer structure as illustrated in FIG. 7, for example. One example of processing in each layer is illustrated as a table 1 below.

TABLE 1

One example of each processing content

| Classification | Network | Activation function | Output ch (depth of feature map) | Convolution filter size | Processing |
|---|---|---|---|---|---|
| Encoder | Stage1 Down sampling | ReLu | 16 | 3 | Convolution (1D) MaxPooling (1D) |
|  | Stage2 Down sampling | ReLu | 8 | 3 | Convolution (1D) MaxPooling (1D) |
|  | Stage3 Down sampling | ReLu | 8 | 3 | Convolution (1D) MaxPooling (1D) |
| Decoder | Stage1 Up sampling | ReLu | 8 | 3 | Convolution (1D) UpSampling (1D) |
|  | Stage2 Up sampling | ReLu | 8 | 3 | Convolution (1D) UpSampling (1D) |
|  | Stage3 Up sampling | ReLu | 16 | 3 | Convolution (1D) UpSampling (1D) |
| Output |  | Sigmoid | 1 | 3 | Convolution (1D) |

Next, the identification model for calculating a prescribed parameter from the feature B will be described. The identification model is a model learned using a plurality of combinations of the feature B and the grade of a tumor as data for learning, and is incorporated into the identification unit 240 such that when the feature B is input to the identification unit 240, the closest grade to the grade to be classified from the feature B is extracted.

In the identification model, as schematically illustrated in FIG. 6, the feature B is divided into a plurality of classifications 45B necessary for a diagnosis, and a grade of a tumor (for example, level 0 to level 4) is calculated from the classifications 45B as parameters 46B. This identification model is incorporated into the identification unit 240.

It should be noted that as for the abovementioned respective CNNs, publicly known software (OSS: Open Source Software) such as TensorFlow (Google LLC (registered trademark)), Chainer (Preferred Networks. Inc. (registered trademark)), and Theano (Universite de Montreal) can be used.

When the neural network is caused to learn, as an error function for minimizing an error between a network output value and target data (training data), generally, an error backpropagation method using a square error function as indicated in the following equation (1) is used.

$$E = \sum_k \frac{(t_k - y_k)^2}{2} \quad (1)$$

tk: training data
yk: network output data

Although k is the number of data, in actual learning, k may generally be the number of batches that is "single bundle" of data to be processed.

Figure 8:
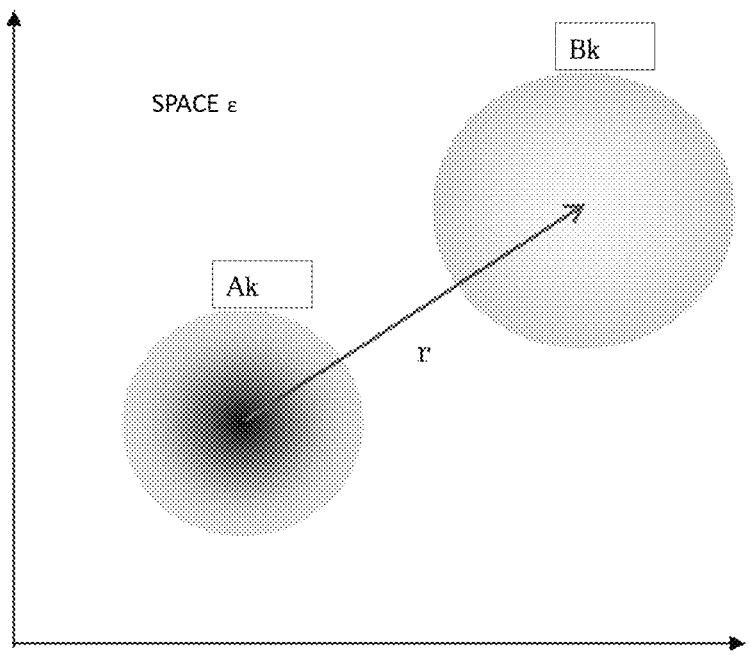
FIG. 8 is a diagram illustrating an example of processing (No. 1) that improves the accuracy of a feature transformation model.

In the learning of the feature transformation model in the embodiment, using any one or a combination of the following error functions enables the accuracy of the prediction model to be improved.
1. Predetermined Space Distance Error
2. Identification Model Error Hereinafter, these error functions will be described.
1. Predetermined Space Distance Error When data of the feature A for learning and data of the feature B for learning are respectively an input (training data) $A_k$ and an output $B_k$, the training data $A_k$ and the output $B_k$ are respectively dimensionally converted and compressed to be mapped in a prescribed space s, as illustrated in FIG. 8. As a mapping method, for example, PCA or t-distributed Stochastic Neighbor Embedding (tSNE) is used. It should be noted that in this diagram, the space ε is a two-dimensional space, but is not limited thereto.

A distance r (for example, between centroids of respective data sets) between the training data $A_k$ and the output $B_k$ on the space ε is added to the error function (1), thereby setting an error function so as to have a small error of the distance r on the space ε. For example, when a transformation function to the space ε is set as g, and a centroid (mean value of coordinates of the respective data) on the space ε is expressed as C, the error function is expressed as the following equation (2).

$$E2 = \sum_k \frac{(C(g(A_k)) - C(g(B_k)))^2}{2} \quad (2)$$

This equation (2) is used as the error function, and learning by the error backpropagation method is conducted.
2. Identification Model Error This method is a method when a feature transformation model and an identification model (a model including, in addition to a model that converts a feature, an identification result performed by the identification unit 240) are learned, an error (loss value) between an output from the identification unit 240 and training data is backpropagated as an error function, thereby minimizing the error of the identification result (see FIG. 9).

Figure 9:
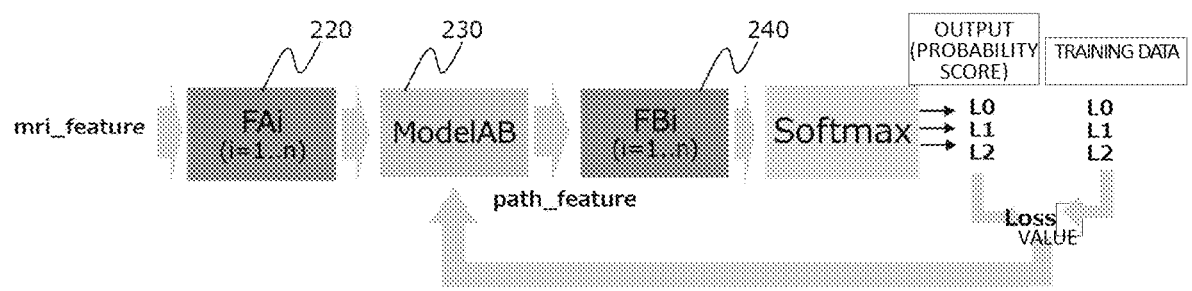
FIG. 9 is a diagram illustrating an example of processing (No. 2) that improves the accuracy of the feature transformation model.

In this method, firstly, using a difference between an output (probability score (softmax layer output (0 to 1))) for each identification class and training data as a loss value, a loss function is set. When the number of classes of the output of the identification result is 3 classes, as illustrated in FIG. 9, for example, a value of an output vector ($y_{L0}$, $y_{L1}$, $y_{L2}$) as the following equation (3) is obtained.

$$\begin{pmatrix} y_{L0} \\ y_{L1} \\ y_{L2} \end{pmatrix} = \begin{pmatrix} 0.6 \\ 0.2 \\ 0.2 \end{pmatrix} \quad (3)$$

Meanwhile, a value of training data vector ($yo_{L0}$, $yo_{L1}$, $yo_{L2}$) as the following equation (4) is obtained.

$$\begin{pmatrix} yo_{L0} \\ yo_{L1} \\ yo_{L2} \end{pmatrix} = \begin{pmatrix} 1 \\ 0 \\ 0 \end{pmatrix} \quad (4)$$

A vector error between an output vector and a training data vector can be defined by an error function as the following equation (5).

$$E3 = -\Sigma_{k=L0}^{L2} yo_k \log y_k \quad (5)$$

When the abovementioned values of the output vector and the training data vector are used, a value of the equation (5)
E3=−(1×log 0.6+0×log 0.2+0×log 0.2)
=−(−0.22)
=0.22
is obtained.

Using the error functions as in the foregoing can make errors in the feature transformation model and the identification model small, and can implement a more highly accurate prediction model. Moreover, weighting may be implemented by combining the abovementioned error functions (2) and (5), and may construct an error function as the following equation (6).

$$E4 = w1*E2 + w2*E3 \quad (6)$$

Here, w1, w2 are respectively weight coefficients (for example, w1=0.5, w2=0.5).
[Image Processing Operation]

Figure 10:
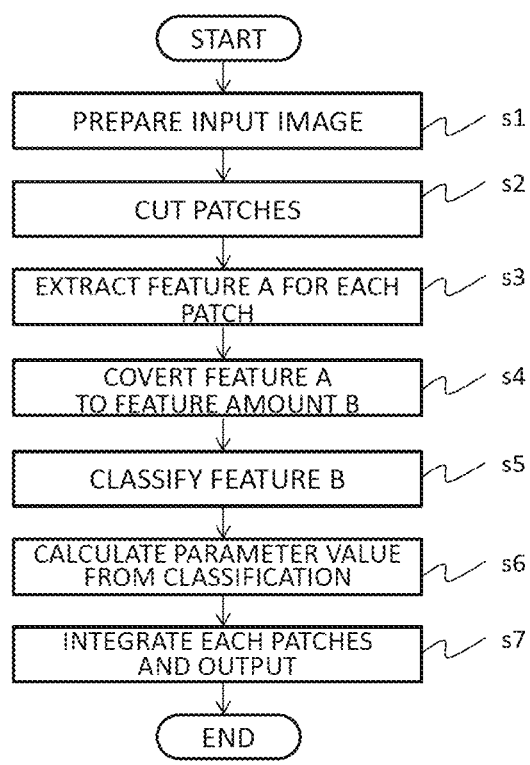
FIG. 10 is a diagram illustrating a flow of an image processing unit in which a learning model is incorporated.

Next, an operation of a flow of the image processing unit 118 in which the abovementioned learned CNNs have been incorporated, with reference to FIG. 10, will be described using a case of cutting a patch as an example.

When the image processing unit 118 receives an image signal from the observation unit 100, the image processing unit 118 firstly prepares the input image 204 to be processed. Specifically, the image reconstruction unit 200 generates image data of the input image 204 from the image signal, and the correction processing unit 201 corrects the image using the generated image data, and outputs the corrected image data to the diagnosis support processing unit 202 and the output unit 120 (s1). Subsequently, the patch processing unit 210 cuts, similarly to when the prediction model is created, all the image data to be processed into patches of a prescribed size (FIG. 4), and passes the patches to the feature extraction unit 220 (s2). The feature extraction unit 220 extracts the feature A of the input image 204 for each patch using the prediction model (s3). The extraction method of the feature A is similar to the method in which a prediction model (FIG. 3) is created, and the feature A from the image 203 for learning.

Next, the feature transformation unit 230 converts the feature A to the feature B using the feature transformation model (FIG. 5) (s4). The identification unit 240 classifies the converted feature B (s5), and calculates a parameter value from the classification (s6). The identification unit 240 acquires the image 205 (see FIG. 11) to which each patch is integrated and the parameter value is reflected, outputs the image data to the output unit 120, and causes the output unit 120 to display the image data (s7).

With the operation in the foregoing, as illustrated in FIG. 11, image data of the image 204 correction-processed by the correction processing unit 201 and image data of the image 205 processed by the diagnosis support processing unit 202 are output to the output unit 120, and either one or both of the images 204 and 205 are displayed.

A display method of a parameter value in the output unit 120 is not limited to the specific method as long as it is possible to cause a user of the image diagnostic device 10 to recognize the parameter value, and examples of the display method can include methods of displaying a mark, a numerical value, and an image.

Figures 11A, 11B:
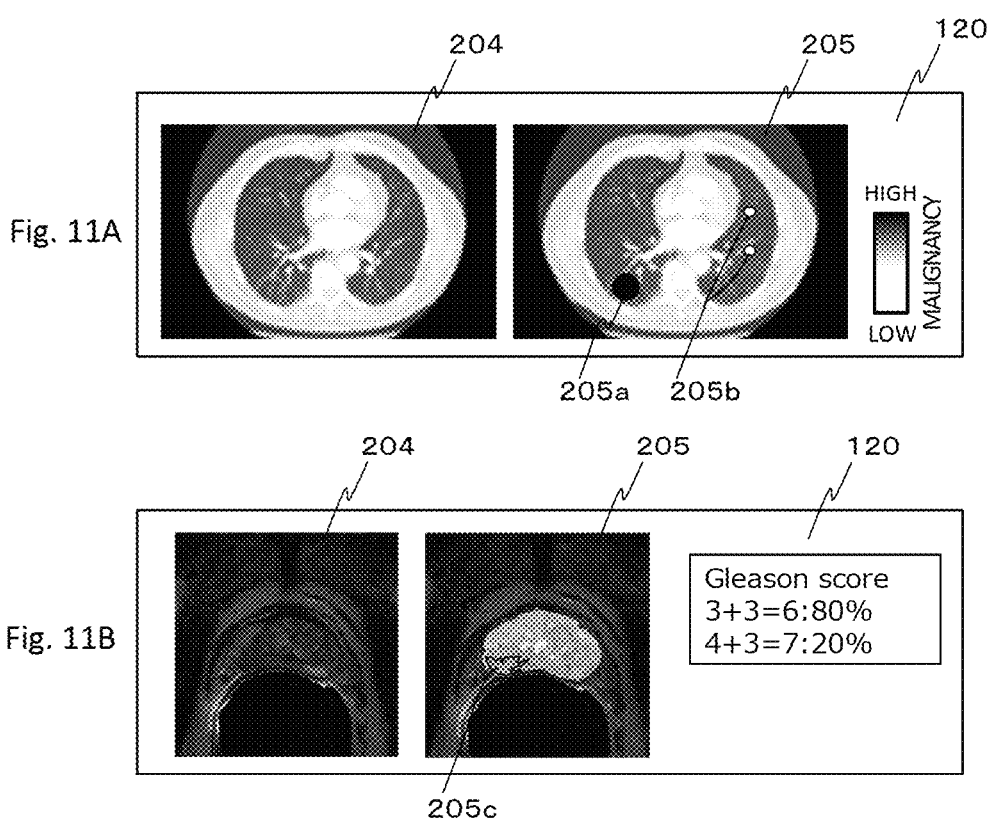
FIGS. 11A and 11B are diagrams illustrating display examples of an input image and an output image.

In a case where the parameter is the malignancy of a tumor, the image 205 can be obtained by superimposing a mark in accordance with the malignancy onto a site having a tumor in the correction image 204. For example, in the image 205 illustrated in FIG. 11A, the color of the mark to be superimposed onto the image varies depending on the malignancy, and a black color is used for a site 205a having a high malignancy and a white color is used for a site 205b having a low malignancy. Moreover, in a case of GS and the like where the parameter is used for the stage calculation of prostate cancer, as illustrated in FIG. 11B, a region 205c where a tumor is present may be presented by being surrounded, or information (numerical values) indicating GS may be displayed. In addition, as illustrated in FIG. 11B, a site where a disease is present may be displayed by a pathological image that can be predicted from the parameter value being superimposed thereon.

As has been described in the foregoing, with the embodiment, it is possible to generate an input image from signals collected by the observation unit, convert the feature A extracted from the input image to the feature B having more detailed information on the image, and calculate a parameter value that is used for a more highly accurate diagnosis from the feature B. Therefore, it is possible to indicate a highly accurate diagnosis result without conducting a detailed examination other than the diagnosis that has used the image diagnostic device.

Moreover, in the embodiment, a relationship of features between different images is caused to be learned, so that, for example, it is possible to medically indicate which portion of the image of the image diagnostic device is watched for determining a feature to be obtained from a pathological image, and to make a determination by a user relative to the diagnosis result more accurately. In other words, it is possible to cause the user to notice a feature that is generally hard to be seen in the image of the image diagnostic device and easy to be missed.

First Modification Example of First Embodiment

Figure 12:
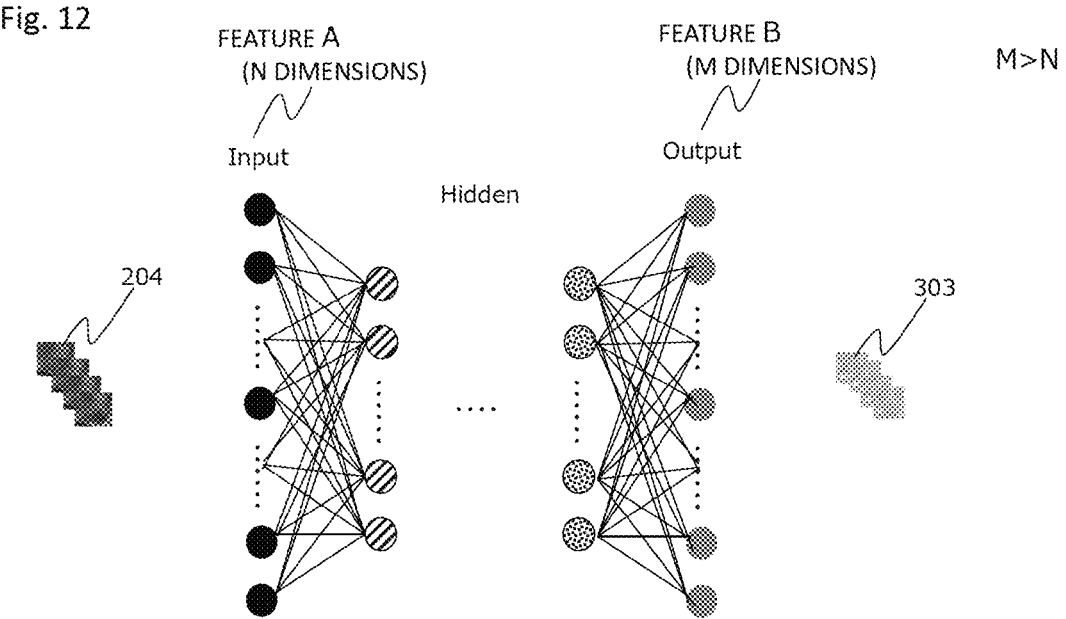
FIG. 12 is a diagram illustrating a configuration of a feature transformation unit in a first modification example of the first embodiment.

The feature A and the feature B have the same dimensions (N dimensions) in the first embodiment, however, the dimensions of the feature A and the feature B may be different. For example, when the feature A has N dimensions and the feature B has M dimensions, as illustrated in FIG. 12, the dimensions of the feature B may be larger than (M>N) or smaller than (M<N) the dimensions of the feature A.

Second Modification Example of First Embodiment

Figure 13:
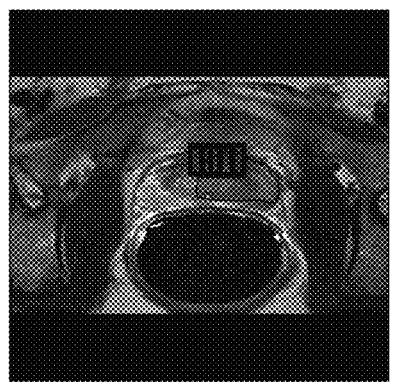
FIG. 13 is a diagram for explaining patch processing in a second modification example of the first embodiment.
Figure 13:
Figure 13:
Figure 13:
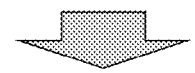
Figure 13:
Figure 13:

In the first embodiment, patches are cut from image data under a condition that each patch is not overlapped with each other, however, the patch processing unit 210 may cut patches such that the adjacent patches are overlapped with each other, as illustrated in FIG. 13. Patches are cut by being overlapped with each other, and the abovementioned CNN processing is performed, whereby it is possible to further improve the image quality of the output image. It should be noted that all the patches are not overlapped with each other, but a part thereof, for example, only patches in the region of interest may be overlapped with each other.

Third Modification Example of First Embodiment

All the patches cut from image data are image-processed in the first embodiment, however, only an image in a region of interest (ROI) may be processed.

Figure 14:
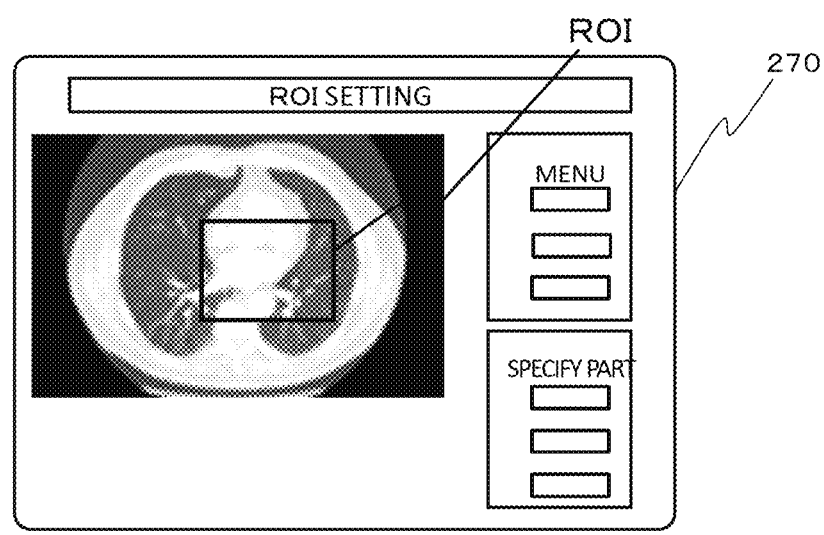
FIG. 14 is a diagram illustrating a screen example of ROI setting in a third modification example of the first embodiment.

In that case, for example, with a UI (ROI setting unit 270) or the like as illustrated in FIG. 14, a user of the image diagnostic device 10 may be caused to set a ROI. When the user sets a ROI, the image processing unit 118 processes, by using the information, only image data in a portion set as the ROI. Therefore, image data in which only the ROI has been converted to have the high image quality is obtained.

With the modification example as in the foregoing, by omitting image processing of a portion that is deviated from the region of interest, it is possible to shorten the processing time as a whole.

Fourth Modification Example of First Embodiment

The case where a parameter (for example, grade of a tumor) is calculated from input image has been described in the first embodiment. However, the type of the parameter that can be output by the image processing unit is not limited to one type. For example, learning models of a plurality of patterns including a learning model in accordance with an examination site of a subject, for breast cancer or stomach cancer, and a learning model in accordance with various kinds of diseases, but not limited to tumor, may be stored in the storage device 121. In that case, a user inputs a diagnosis site or a name of the disease that the user is desired to diagnose from the input unit 119 (see FIG. 15), whereby the image processing unit may select a learning model to be used in the processing in accordance with the input content, and calculate a parameter using the selected learning model.

The embodiment and the modification examples thereof that are applicable independent of the type of the observation unit have been described in the foregoing. Subsequently, an embodiment for each modality will be described.

Second Embodiment

An embodiment in which the invention is applied to an MRI device will be described. As illustrated in FIG. 15, an MRI device 10B includes an MR observation unit 100B that corresponds to the observation unit 100 in the first embodiment, and a reconstruction unit 106B that performs a computation such as image reconstruction using a nuclear magnetic resonance signal received from the MR observation unit 100B.

The MR observation unit 100B includes the configuration similar to that of the conventional MRI device, and measures a magnetic resonance signal of an examination object, and acquires k space data including the magnetic resonance signal. Specifically, the MR observation unit 100B is provided with a static magnetic field generation unit 102 that generates a static magnetic field, a gradient magnetic field generation unit 103 including gradient magnetic field coils 109 that generate gradient magnetic fields in three axial directions in the static magnetic field space, a transmission unit 104 including a transmission coil 114a that applies a high frequency magnetic field to a subject 101 inside the static magnetic field space, a reception unit 105 including a reception coil 114b that receives a nuclear magnetic resonance signal to be generated from the subject 101, a sequencer 107 that controls operations of the gradient magnetic field generation unit 103, and the transmission unit 104 and the reception unit 105 in accordance with a prescribed pulse sequence.

The gradient magnetic field generation unit 103 is provided with a gradient magnetic field power supply 110 for driving the gradient magnetic field coils 109, and the transmission unit 104 is provided with a high frequency generator 111 that provides a prescribed high frequency signal to the transmission coil 114a, and causes the transmission coil 114a to emit an electromagnetic wave of a nuclear magnetic resonance frequency, an amplifier 113, a modulator 112, and the like. Moreover, the reception unit 105 includes an amplifier 115 that amplifies a signal detected by the reception coil 114b, a quadrature detector 116, an A/D converter 117 for transformation to a digital signal, and the like.

The reconstruction unit 106B is provided with an image processing unit 118B that performs the processing similar to that of the image processing unit 118 in the first embodiment using a nuclear magnetic resonance signal (k space data) acquired by the MR observation unit 100B, and the input unit 119 with which a command of information necessary for each unit is input, the output unit 120 that displays the created image or a UI, and the storage device 121 that stores therein the nuclear magnetic resonance signals acquired by the MR observation unit 100B, data in the course of the calculation, and numerical values necessary for the calculation, such as parameters.

The function of the reconstruction unit 106B is implemented by a memory and software mounted to a CPU or a GPU. It should be noted that a part of the image processing unit 118B may be configured by hardware.

The configuration and the function of the image processing unit 118B are similar to those of the image processing unit 118 in the first embodiment, and is provided with, with reference to FIG. 1, the image reconstruction unit 200, the correction processing unit 201, and the diagnosis support processing unit 202. Moreover, the diagnosis support processing unit 202 is provided with, as illustrated in FIG. 2, the patch processing unit 210, the feature extraction unit 220, the feature transformation unit 230, and the identification unit 240.

As for data for learning of the feature extraction unit 220 in the embodiment, data of an MR image and benign-malignant information of the image are prepared. As for data for learning of the feature transformation unit 230, combination data of the feature A and the feature B is prepared. Moreover, as for data for learning of the identification unit 240, data of the MR image that is caused to be learned by the feature extraction unit 220, and combination data of pathological image data of the same site and a parameter value (grade of cancer and the like) are prepared.

In the imaging, the MR observation unit 100B collects k space data by an arbitrary imaging method, and transmits the k space data to the image processing unit 118B. The image processing unit 118B performs the processing similar to that in the first embodiment. The image reconstruction unit 200 firstly generates image data of an MR image in a real space from k space data, and the correction processing unit 201 performs correction processing of the generated MR image, and inputs the correction-processed MR image to the diagnosis support processing unit 202. The patch processing unit 210 performs patch processing of the input MR image, and the feature extraction unit 220 extracts the feature A for each patch from image data of the MR image. The feature transformation unit 230 converts the feature A to the feature B. The identification unit 240 calculates a parameter value from the feature B, integrates the patches to obtain an MR image, and outputs the parameter value and MR image data to the output unit 120.

In the embodiment, by applying the modification examples of the first embodiment, the abovementioned processing by the image processing unit 118B may be performed on only a desired region in the MR image, and patches may be cut by being overlapped with each other.

With the image diagnostic device (MRI device) in the embodiment, it is possible to calculate a parameter value to be used for a highly accurate diagnosis from an input image (MR image) of a subject, and thus to obtain an image indicating a highly accurate diagnosis result without conducting a detailed examination other than the diagnosis that has used the image diagnostic device. Therefore, using the MRI device in the embodiment enables a diagnosis equivalent to the pathological diagnosis, without conducting the pathological examination, for example, so that it is possible to conduct a highly accurate diagnosis while reducing a physical burden to a patient.

Third Embodiment

Figure 16:
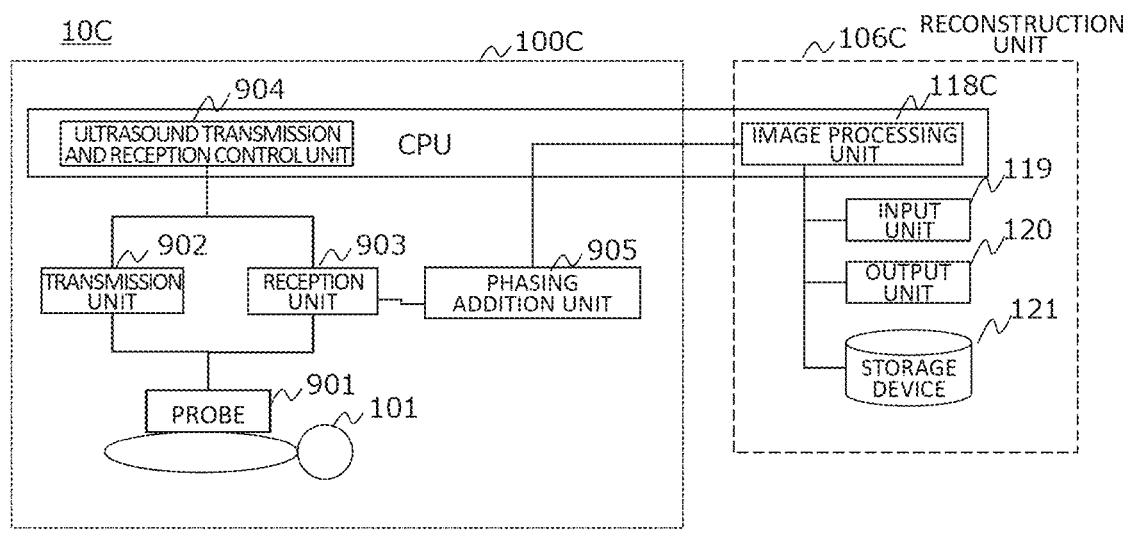
FIG. 16 is a diagram illustrating an overall configuration of an image diagnostic device (ultrasound imaging device) in a third embodiment.

An embodiment in which the invention is applied to an ultrasound imaging device will be described. FIG. 16 illustrates an overall overview of an ultrasound imaging device 10C. This device includes an ultrasound observation unit 100C corresponding to the observation unit 100 in the first embodiment, and a reconstruction unit 106C that performs a computation such as image reconstruction using an ultrasound signal received from the ultrasound observation unit 100C.

The ultrasound observation unit 100C includes the configuration similar to that of the conventional ultrasound imaging device, and is provided with an ultrasound probe 901 that generates ultrasound, a transmission unit 902 that sends an ultrasound drive signal to the probe 901, an ultrasound reception unit 903 that receives an ultrasound signal (RF signal) from the probe 901, a phasing addition unit 905 that performs phasing addition (beam forming) of the signal received by the ultrasound reception unit 903, and an ultrasound transmission and reception control unit 904 that controls the ultrasound transmission unit 902 and the ultrasound reception unit 903.

The reconstruction unit 106C is provided with an image processing unit 118C that generates an ultrasound image from the ultrasound signal acquired by the observation unit 100C and performs the processing similar to that of the image processing unit 118 in the first embodiment, the input unit 119, the output unit 120, and the storage device 121. The reconstruction unit 106C may further be provided with a Doppler processing unit (which is not illustrated) or the like. In the illustrated configuration example, the ultrasound transmission and reception control unit 904 and the image processing unit 118C are constructed in one CPU, however, the ultrasound transmission and reception control unit 904 may be constructed in a CPU different from that of the image processing unit 118C, or may be a combination of hardware such as a transmission and reception circuit and control software.

The configuration and the function of the image processing unit 118C are similar to those of the image processing unit 118 in the first embodiment, and is provided with, as illustrated in FIG. 1, the image reconstruction unit 200, the correction processing unit 201, and the diagnosis support processing unit 202. Moreover, the diagnosis support processing unit 202 is provided with, as illustrated in FIG. 2, the patch processing unit 210, the feature extraction unit 220, the feature transformation unit 230, and the identification unit 240.

As for data for learning of the feature extraction unit 220 in the embodiment, data of an ultrasound image and benign-malignant information of the image are prepared. As for data for learning of the feature transformation unit 230, combination data of the feature A and the feature B is prepared. Moreover, as for data for learning of the identification unit 240, data of an ultrasound image that is caused to be learned by the feature extraction unit 220, and combination data of a pathological image of the same site and a parameter value (for example, grade of cancer) are prepared.

In the imaging, ultrasound received by the probe 901 in the ultrasound observation unit 100C is subjected to phasing addition, and an ultrasound signal is transmitted to the image processing unit 118C. The image processing unit 118C performs the processing similar to that in the first embodiment. The image reconstruction unit 200 firstly generates an ultrasound image from the ultrasound signal, and the correction processing unit 201 performs correction processing of the generated ultrasound image, and inputs the correction-processed ultrasound image to the diagnosis support processing unit 202. The patch processing unit 210 performs patch processing of the input ultrasound image, and the feature extraction unit 220 extracts the feature A from image data of the ultrasound image. The feature transformation unit 230 converts the feature A to the feature B. The identification unit 240 calculates a parameter value from the feature B, integrates the patches to obtain an ultrasound image, and outputs the parameter value and ultrasound image data to the output unit 120. Also, in the embodiment, it is possible to apply the modification examples having been described in the first embodiment, as appropriate.

With the ultrasound imaging device in the embodiment, it is possible to calculate a parameter value to be used for a highly accurate diagnosis from an ultrasound image, and thus to obtain a highly accurate diagnosis result without conducting a detailed examination other than the diagnosis that has used the ultrasound imaging device.

Fourth Embodiment

Figure 17:
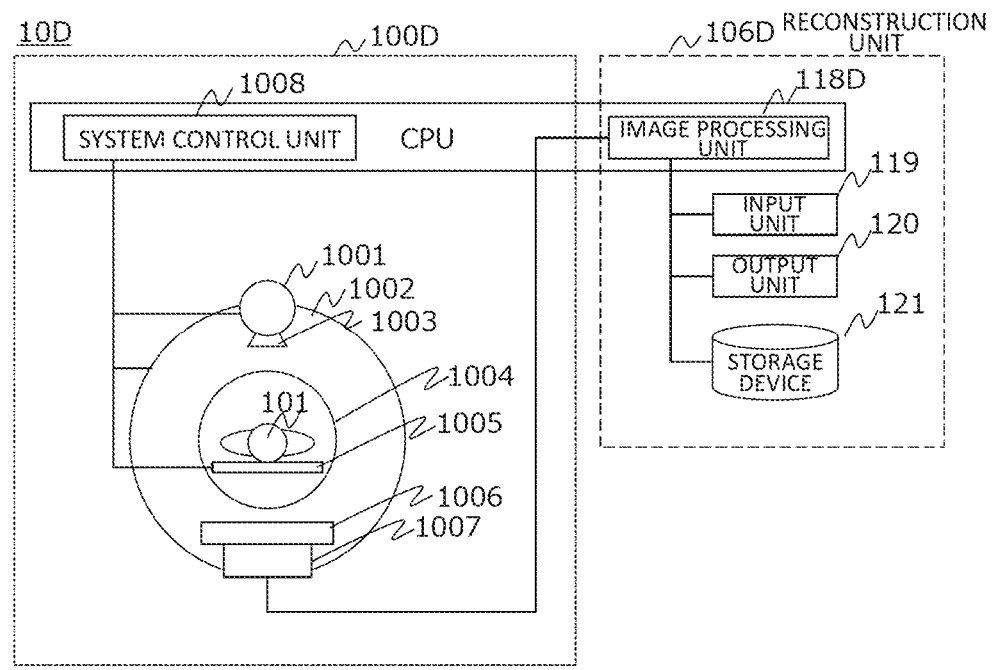
FIG. 17 is a diagram illustrating an overall configuration of an image diagnostic device (CT device) in a fourth embodiment.

An embodiment in which the invention is applied to a CT device will be described. FIG. 17 illustrates an overall overview of a CT device 10D. This device is roughly divided into a CT observation unit 100D corresponding to the observation unit 100 in the first embodiment, and a reconstruction unit 106D that performs a computation such as image reconstruction using a CT image signal received from the CT observation unit 100D.

The CT observation unit 100D is provided with the configuration similar to that of the conventional CT device, and is provided with an X-ray source 1001 that emits X-rays to the subject 101, a collimator 1003 that limits an irradiation range of the X-rays, an X-ray detector 1006 that detects transmitted X-rays passed through the subject 101, a rotation plate 1002 that includes an opening 1004 in the center thereof and supports the X-ray source 1001 and the X-ray detector 1006 at facing positions, a bed 1005 on which the subject 101 is mounted in a space inside the opening 1004, a data collection unit 1007 that collects outputs from the X-ray detector 1006 for each projection data, and a system control unit 1008 that controls operations of the respective elements constituting the CT observation unit 100D.

The reconstruction unit 106D is provided with an image processing unit 118D that performs the processing similar to that of the image processing unit 118 in the first embodiment to a tomographic image (CT image) generated by the CT observation unit 100D, the input unit 119, the output unit 120, and the storage device 121. Moreover, in the illustrated configuration example, the system control unit 1008 and the image processing unit 118D are constructed in one CPU, however, the system control unit 1008 may be constructed in a CPU different from that of the image processing unit 118D, or may be a combination of hardware such as a transmission and reception circuit and control software. Similarly, a part of the function of the reconstruction unit 106D can be configured as hardware.

The function of the image processing unit 118D is similar to that of the image processing unit 118 in the first embodiment, and is provided with, as illustrated in FIG. 1, the image reconstruction unit 200, the correction processing unit 201, and the diagnosis support processing unit 202. Moreover, the diagnosis support processing unit 202 is provided with, as illustrated in FIG. 2, the patch processing unit 210, the feature extraction unit 220, the feature transformation unit 230, and the identification unit 240.

As for data for learning of the feature extraction unit 220 in the embodiment, data of a CT image and benign-malignant information of the image are prepared. As for data for learning of the feature transformation unit 230, combination data of the feature A and the feature B is prepared. Moreover, as for data for learning of the identification unit 240, data of a CT image that is caused to be learned by the feature extraction unit 220, and combination data of a pathological image of the same site, and a parameter value (for example, grade of cancer) are used.

In the imaging, the data collection unit 1007 collects X-ray signals of the transmitted X-rays detected by the X-ray detector 1006 in the CT observation unit 100D, and transmits the X-ray signals to the image processing unit 118D. In the image processing unit 118D, similar to the first embodiment, the image reconstruction unit 200 firstly generates a CT image, and the correction processing unit 201 performs correction processing of the generated CT image, and inputs the correction-processed CT image to the diagnosis support processing unit 202. The patch processing unit 210 performs patch processing of the input CT image, and the feature extraction unit 220 extracts the feature A from the CT image. The feature transformation unit 230 converts the feature A to the feature B. The identification unit 240 calculates a parameter value from the converted feature B, integrates the patches to obtain a CT image, and outputs the parameter value and CT image data to the output unit 120. Also, in the embodiment, it is possible to apply the modification examples having been described in the first embodiment, as appropriate.

With the CT device in the embodiment, it is possible to calculate a parameter value to be used for a highly accurate diagnosis from a CT image, and thus to obtain a highly accurate diagnosis result without conducting a detailed examination other than the diagnosis that has used the CT device.

What is claimed is:

1. An image diagnostic device, comprising:
an imaging device that collects an image signal of an examination object;
a memory; and
a processor communicatively coupled to the input device and the memory, wherein the processor is configured to:
generate first image data from the image signal,
perform image processing of the first image data,
extract a first feature from the first image data,
convert the first feature to a second feature to be extracted from second image data,
learn a prediction model using a plurality of combinations of the first image data and the first feature,
learn an error function for minimizing an error between an output value and target data,
learn a feature transformation model using the plurality of the combinations of the first feature, the second feature and the error,
classify the second feature into a plurality of classifications,
calculate a parameter value using the plurality of classifications of the second feature, and
output image data including the first feature, the second feature and the parameter value,
wherein in the error function includes
the first feature and the second feature are used as the target data,
the target data is dimensionally converted into converted target data,
the converted target data is compressed and mapped into a predetermined space, to create mapped converted target data and
a distance is determined between the mapped converted target data the first feature used as the target data to create the error.

2. The image diagnostic device according to claim 1, wherein the memory includes an identification model learned using a plurality of combinations of the second feature and the parameter value.

3. The image diagnostic device according to claim 1, wherein
the second image data is image data of a pathological image of the examination object, and
the second feature includes a feature of the pathological image.

4. The image diagnostic device according to claim 1, wherein the processor includes two networks of an encoder and a decoder, and when the first feature is input to the encoder, the second feature is output from the decoder.

5. The image diagnostic device according to claim 1, wherein the error of a distance between the first feature and the second feature becomes small, by an error backpropagation method using the error function.

6. The image diagnostic device according to claim 1, wherein the processor includes a model learned such that an error between an output of the parameter value calculated by the identification unit and training data becomes small, by the error backpropagation method using a prescribed error function.

7. The image diagnostic device according to claim 1, wherein the error of a distance between the first feature and the second feature that is mapped on a prescribed space becomes small, and an error between an output of the parameter value calculated by the identification unit and training data becomes small, by the error backpropagation method using the error function.

8. The image diagnostic device according to claim 1, wherein
the processor is further configured to:
reconstruct an image from the image signal; and
correct the image generated, and
extracts the first feature using image data of the corrected image as the first image data.

9. The image diagnostic device according to claim 1, further comprising an output unit that displays the image processed, wherein
the processor causes the output unit to display an image of the first image data and information on the parameter value by being superimposed on or in parallel with each other.

10. The image diagnostic device according to claim 9, wherein the information on the parameter value includes an image of the second image data corresponding to the parameter value.

11. The image diagnostic device according to claim 10, wherein the image of the second image data is a pathological image, among sites to be examined image signals of which have been collected by the imaging device, at the site the same as the site with a disease.

12. The image diagnostic device according to claim 1, wherein
the first feature and the second feature respectively have a plurality of dimensions, and
the second feature has a dimension number larger than that of the first feature.

13. The image diagnostic device according to claim 1, wherein
the processor is further configured to cut image data of at least one patch from the image data collected, and
extract the first feature from the cut image data of at least one patch.

14. The image diagnostic device according to claim 1, the processor is further configured to sets a region of interest in the image data of the examination object, and
process image data of the region set.

15. The image diagnostic device according to claim 1, wherein
the imaging device is an MR observation unit that measures a magnetic resonance signal of an examination object, and acquires k space data including the magnetic resonance signal, and the processor performs image reconstruction using the k space data acquired by the MR observation unit.

16. The image diagnostic device according to claim 1, wherein
the imaging device is an ultrasound observation unit that acquires an ultrasound signal of an examination object, and
the processor generates image data of an ultrasound image from the ultrasound signal, and performs the image reconstruction using the image data.

17. The image diagnostic device according to claim 1, wherein
the imaging device is a CT observation unit that acquires an X-ray signal passed through an examination object, and
the processor generates image data of a tomographic image from the X-ray signal acquired by the CT observation unit, and performs the image reconstruction using the generated image data.

18. The image diagnostic device according to claim 1, wherein the prediction model and the feature transformation model are stored in a cloud connected to the imaging device via a network.

19. An image processing method, comprising:
generating first image data from an image signal of an examination object acquired by an image diagnostic device;
extracting, using a prediction model learned by a plurality of combinations of the first image data and a first feature, the first feature from the first image data;
learning an error function for minimizing an error between an output value and target data;
converting, using a feature transformation model learned by a plurality of combinations of the first feature, the error, and a second feature to be extracted from second image data, the first feature to the second feature;
classifying the second feature into a plurality of classifications,
calculating a parameter value using the plurality of classifications of the second feature; and
outputting image data including the first feature, the second feature and the parameter value, and
wherein in the error function includes
using the first feature and the second feature as the target data,
dimensionally converting the target data into converted target data,
compressing the converted target data and mapping the compressed converted target data into a predetermined space, to create mapped converted target data, and
determining a distance between the mapped converted target data the first feature used as the target data to create the error.

20. A non-transitory computer-readable medium storing a program that, when executed by a processor, included in a computer, causes the processor to:
generating first image data from an image signal of an examination object acquired by an image diagnostic device;
extracting, using a prediction model learned by a plurality of combinations of the first image data and a first feature, the first feature from the first image data;
learning an error function for minimizing an error between an output value and target data;
converting, using a feature transformation model learned by a plurality of combinations of the first feature, the error, and a second feature to be extracted from second image data, the first feature to the second feature;
classifying the second feature into a plurality of classifications,
calculating a parameter value using the plurality of classifications of the second feature; and
outputting image data including the first feature, the second feature and the parameter value, and
wherein in the error function includes
using the first feature and the second feature as the target data,
dimensionally converting the target data into converted target data,
compressing the converted target data and mapping the compressed converted target data into a predetermined space, to create mapped converted target data, and
determining a distance between the mapped converted target data the first feature used as the target data to create the error.

* * * * *